(12) United States Patent
Bro (10) Patent No.: US 11,051,961 B2
(45) Date of Patent: Jul. 6, 2021

(54) DEPLOYMENT HANDLE WITH STABILIZING RAIL FOR A PRE-LOADED PROSTHESIS DELIVERY DEVICE

(71) Applicant: COOK MEDICAL TECHNOLOGIES LLC, Bloomington, IN (US)

(72) Inventor: Kristoffer Vandborg Bro, Aarhus N. (DK)

(73) Assignee: Cook Medical Technologies LLC, Bloomington, IN (US)

( * ) Notice: Subject to any disclaimer, the term of this patent is extended or adjusted under 35 U.S.C. 154(b) by 154 days.

(21) Appl. No.: 16/534,003

(22) Filed: Aug. 7, 2019

(65) Prior Publication Data
US 2020/0054468 A1     Feb. 20, 2020

Related U.S. Application Data

(60) Provisional application No. 62/764,870, filed on Aug. 15, 2018.

(51) Int. Cl.
*A61F 2/966* (2013.01)
*A61M 29/02* (2006.01)
*A61F 2/95* (2013.01)

(52) U.S. Cl.
CPC .............. *A61F 2/966* (2013.01); *A61M 29/02* (2013.01); *A61F 2/9517* (2020.05); *A61F 2002/9505* (2013.01)

(58) Field of Classification Search
CPC ..................... A61F 2/966; A61F 2/9517; A61F 2002/9505; A61F 2/954; A61F 2/95; A61F 2002/9511; A61M 29/02; A61M 25/1018
See application file for complete search history.

(56) References Cited

FOREIGN PATENT DOCUMENTS

WO       WO 00/61035 A1     10/2000

OTHER PUBLICATIONS

Examination Report for Great Britain Application No. 1813315.7, dated Jan. 25, 2019, 7 pages.
Examination Report for Great Britain Application No. 1813315.7, dated Aug. 21, 2019, 2 pages.

*Primary Examiner* — George J Ulsh
*Assistant Examiner* — Andrew P. Restaino
(74) *Attorney, Agent, or Firm* — Brinks Gilson & Lione (57) ABSTRACT

A handle assembly for a prosthesis delivery device is disclosed. The handle assembly has a proximal gripping portion and a stationary gripping portion. At least one rail extends distally from the proximal gripping portion through the stationary gripping portion. The proximal gripping portion is distally moveable along a longitudinal axis towards the stationary gripping portion from a first pre-deployment position to a second position. The at least one rail extends proximally from the stationary gripping portion when the proximal gripping portion is in a first pre-deployment position and distally from the stationary gripping portion when the proximal gripping portion is in a second position. The at least one rail is configured to prevent the build-up of torque along the length of the delivery device as well as prevent the build-up of torque among the various components of the handle assembly including the proximal gripping portion and the stationary gripping portion.

20 Claims, 7 Drawing Sheets

DEPLOYMENT HANDLE WITH STABILIZING RAIL FOR A PRE-LOADED PROSTHESIS DELIVERY DEVICE

RELATED APPLICATIONS

The present application claims the benefit of the filing date under 35 U.S.C. § 119(e) of Provisional U.S. Patent Application Ser. No. 62/764,870, filed Aug. 15, 2018, which is hereby incorporated by reference.

TECHNICAL FIELD

This invention relates generally to medical devices and methods of use, and more particularly, to an endovascular prosthesis delivery device handle and methods for placement and deployment of a prosthesis in the lumen of a vessel.

BACKGROUND

An endovascular prosthesis, such as a stent, stent graft, vena cava filter or occlusion device, may be inserted into an anatomical vessel or duct for various purposes. For example, a stent graft may be delivered intraluminally from the femoral artery for treatment of vasculature in the human or animal body to bypass a repair or defect in the vasculature or to maintain or restore patency in a formerly blocked or constricted passageway. The stent graft may extend proximally and/or distally away from a vascular defect, including a diseased portion of an aneurysm or dissection, and engage a healthy portion of a vessel wall.

A stent graft to be implanted may be coupled to a delivery device in a compressed state and then released from the delivery device so as to expand within the vessel. The delivery device may then be withdrawn, leaving the stent graft in position within the vessel. The steps to carry out the deployment of the stent graft may occur in a pre-determined deployment sequence. For example, the delivery device may first be positioned within the vessel, and then the sheath retracted to allow the stent graft to at least partially expand. Further steps may then be performed, such as release of one or more trigger wires, for example, that facilitate release of one or both ends of the stent graft, to deploy an anchoring stent, and the like. In most cases, it is desirable that such deployment steps follow a specific order as instructed by the manufacturer of the device.

Positioning and placement of the stent graft within a vessel lumen often requires the user to manipulate and rotate the handle of the delivery device to locate the stent graft at a particular, pre-determined location during a procedure. Thus, it is advantageous and desirable to provide a delivery device having a sturdy and stable handle, such that manipulation, rotation and movement of the handle at the distal end of the delivery device resists twisting and torque, resulting in the accurate corresponding movement of the stent graft at the proximal end of the delivery device to ensure precise placement of the stent graft with the vessel.

SUMMARY

The present disclosure provides a handle assembly for a delivery system for delivering and deploying an endovascular graft.

In one example, a handle assembly includes a proximal gripping portion and a stationary gripping portion, with at least one rail extending distally from the proximal gripping portion and through at least a portion of the stationary gripping portion. The proximal gripping portion is distally moveable along a longitudinal axis towards the stationary gripping portion from a first pre-deployment position to a second position. The at least one rail extends proximally from the stationary gripping portion when the proximal gripping portion is in a first pre-deployment position. The at least one rail extends distally from the stationary gripping portion when the proximal gripping portion is in a second position.

In another example, a delivery system includes an inner cannula having a proximal end and a distal end. A prosthesis is releasably coupled to the proximal end of the inner cannula. A handle assembly is disposed about the distal end of the inner cannula. The handle assembly includes a proximal gripping portion and a stationary gripping portion, with at least one rail extending distally from the proximal gripping portion. The proximal gripping portion is longitudinally moveable towards the stationary gripping portion from a first pre-deployment position to a second position. The at least one rail extends proximally from the stationary gripping portion when the proximal gripping portion is in a first pre-deployment position. The at least one rail extends distally from the stationary gripping portion when the proximal gripping portion is in a second position. A sheath is coupled to and extends proximally from the proximal gripping portion. The sheath is disposed about the prosthesis when the proximal gripping portion is in the first pre-deployment position. The sheath is retracted to expose at least a portion of the stent graft when the proximal gripping portion is in the second position.

In a further example, a method for delivering an endovascular prosthesis is disclosed. The method includes providing a delivery device having a proximal end and a distal end. A prosthesis is releasably coupled to the proximal end of an inner cannula. A handle assembly is disposed about the distal end of the inner cannula. In such examples, a handle assembly includes a proximal gripping portion and a stationary gripping portion, with at least one rail extending distally from the proximal gripping portion. The proximal gripping portion is longitudinally moveable towards the stationary gripping portion from a first pre-deployment position to a second position. The at least one rail extends proximally from the stationary gripping portion when the proximal gripping portion is in a first pre-deployment position. The at least one rail extends distally from the stationary gripping portion when the proximal gripping portion is in a second position. At least one trigger wire release mechanism is disposed upon the at least one rail. This method also includes moving the proximal gripping portion from the first pre-deployment position to the second position to retract a sheath coupled to the proximal gripping portion and expose at least a portion of the prosthesis. This method further includes moving a trigger wire release mechanism distally upon the at least one rail to retract and release at least one trigger wire from the prosthesis.

BRIEF DESCRIPTION OF THE DRAWINGS

Embodiments of the present invention are described below, by way of example only, with reference to the accompanying drawings, in which.

DETAILED DESCRIPTION

In this description, when referring to a prosthesis delivery device, proximal refers to the part of the delivery device that is furthest from the device operator and intended for insertion in a patient's body and distal refers to the part of the delivery device closest to the device operator. With regard to the prosthesis, the term proximal refers to that part of the prosthesis that is closest to the proximal end of the delivery device and distal refers to the opposite end of the prosthesis. Reference to coupling or connection of components, unless specified otherwise, includes direct connection as well as connection through intervening components.

In general and described in more detail below with reference to the reference numbers and Figures, the delivery device 2 includes a proximal end 4 and a distal end 6. A handle assembly 8 is located adjacent the distal end 6 of the delivery device 2.

The delivery device 2 and handle assembly 8 disclosed herein are capable of use with a variety of prostheses. A prosthesis, such as a stent graft, may be disposed on a stent graft retention region 20 at a proximal end 4 of the delivery device 2. The delivery device 2 and handle assembly 8 disclosed herein are also capable of use with a variety of coupling methods for coupling a stent graft 56 to a stent retention region 20 of a delivery device 2, including, but not limited to, one or more trigger wires and diameter reducing ties, as would be understood by one of ordinary skill in the art.

Figure 1:
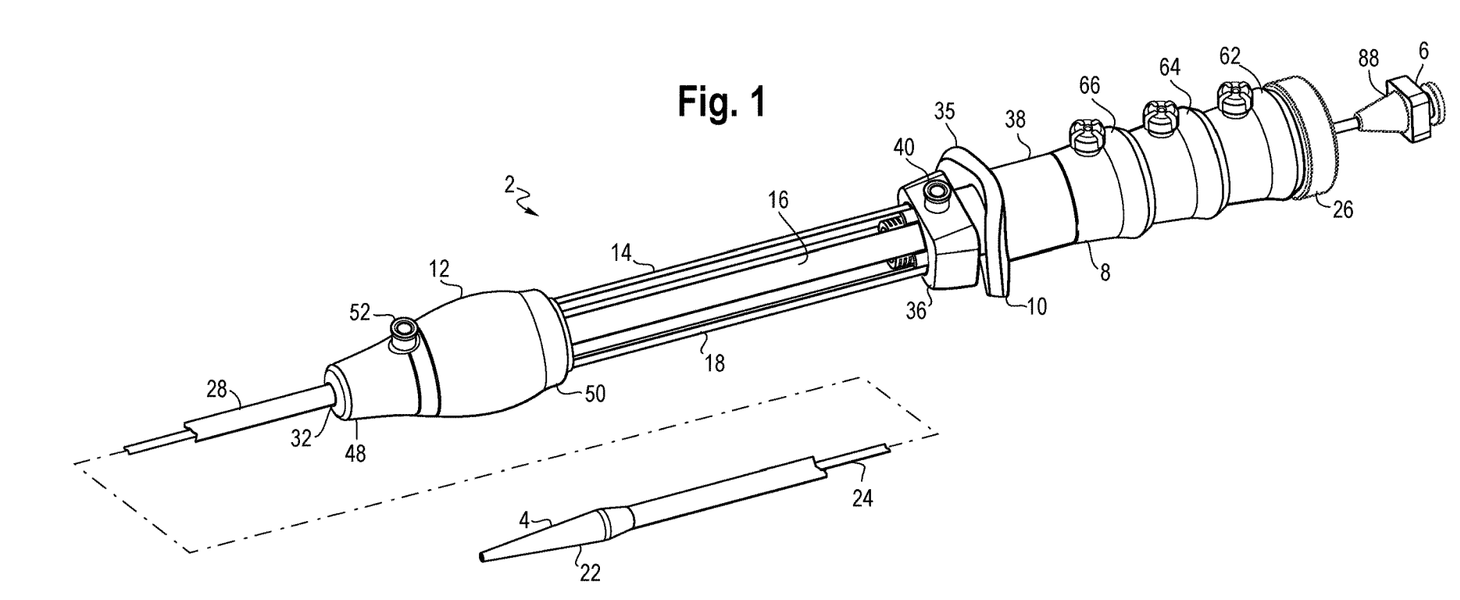
FIG. 1 is a side perspective view of a prosthesis delivery device in pre-deployment configuration with an example of a handle assembly at the distal end and a nose cone dilator at the proximal end.

A delivery device 2 is shown in FIG. 1, in pre-deployment configuration. The proximal end 4 of the delivery device 2 includes a stent graft retention region 20 and a tapered nose cone dilator 22. The nose cone dilator 22 has a proximal tip and a reverse distal taper at its distal end. The surface of the nose cone dilator 22 provides a smooth tapered surface to facilitate entry into and movement through a body vessel. A nose cone dilator 22 may include radiopaque material or be equipped with a radiopaque marker (not shown) to facilitate visualization of the nose cone dilator 22 in use.

Figure 2:
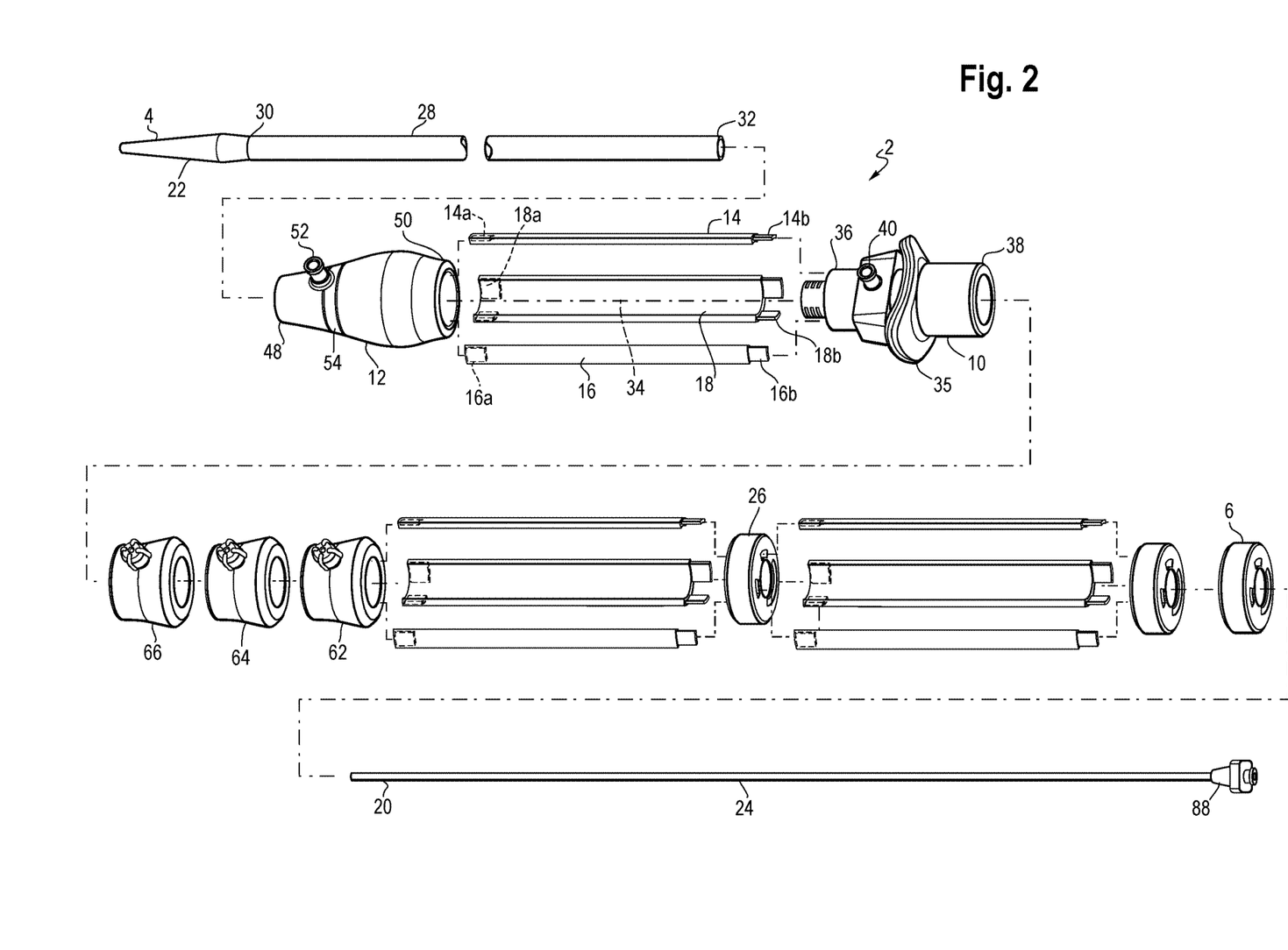
FIG. 2 is an exploded view of one example of a prosthesis delivery device.
Figure 3:
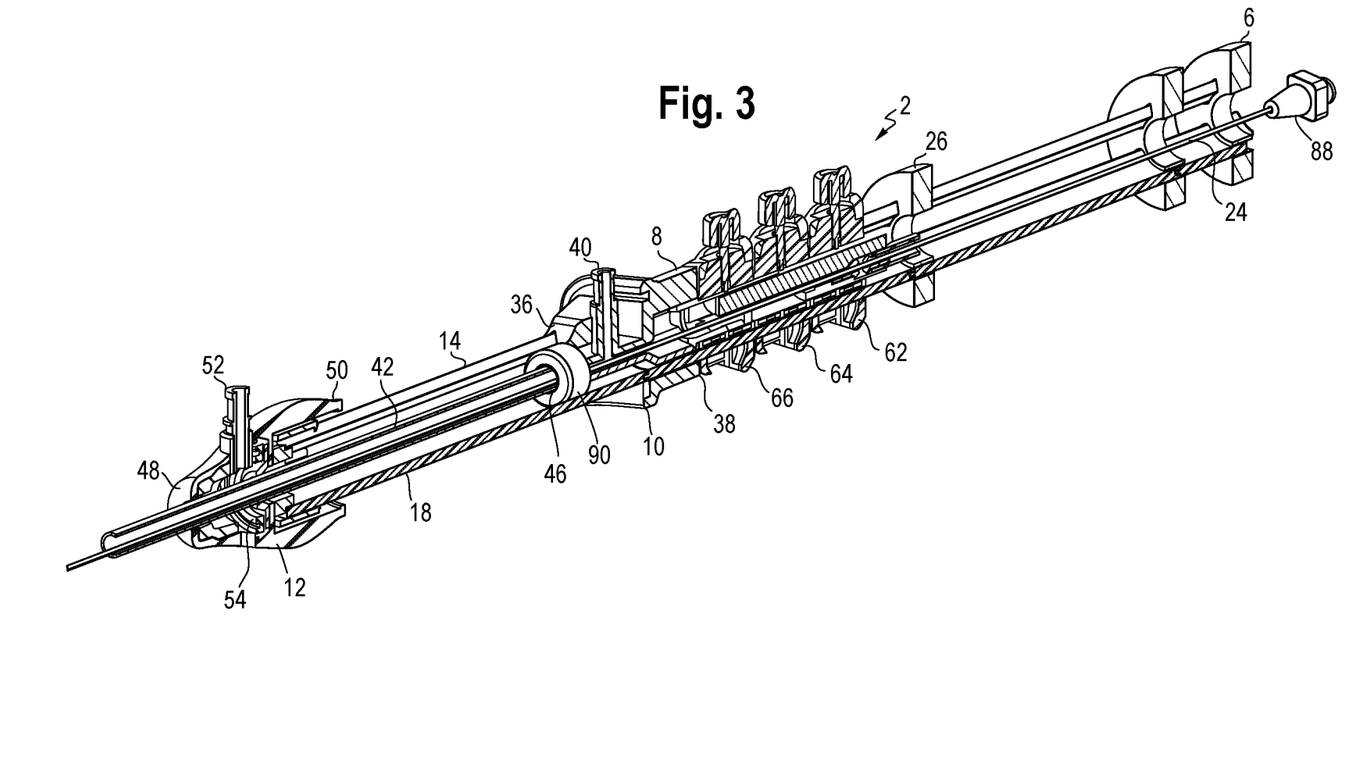
FIG. 3 is a side sectional view of an example of a handle assembly.

As shown generally in FIG. 2, an inner cannula 24 extends the longitudinal length of the delivery device 2, from a luer adapter 88 at the distal end 6 of the delivery device 2 to the tapered nose cone dilator 22 at the proximal end 4 of the delivery device 2. As shown in FIG. 3, the inner cannula 24 has an inner lumen which may accommodate a guide wire for tracking the delivery device 2 to a desired position within a patient's vasculature and which may be used for flushing or injection of fluids. The inner cannula 24 may be made of a variety of suitable materials including a flexible material, polymer, metal, and/or alloy, for example, nitinol or stainless steel, and may be either straight or have a curve imparted to a portion of it.

Handle assembly 8 generally includes a stationary gripping portion 10 and a proximal gripping portion 12. The proximal gripping portion 12 is proximal to the stationary gripping portion 10. A user may hold the stationary gripping portion 10 while manipulating the proximal gripping portion 12 (such as during sheath 28 retraction during deployment). Distal longitudinal movement of the proximal gripping portion 12 causes the sheath 28 to retract distally and expose a portion of a stent graft 56. As shown in FIG. 2, a longitudinal axis 34 extends between and beyond the stationary gripping portion 10 and the proximal gripping portion 12.

Each of the stationary gripping portion 10 and the proximal gripping portion 12 may be ergonomically shaped for user comfort and may be covered in a layer of softer plastic or rubber or have a gripping surface to ensure a stable grip. Each of the stationary gripping portion 10 and the proximal gripping portion 12 may be injection molded as a single unitary structure, or alternatively, may comprise parts that clam shell, lock, snap fit, or are otherwise securable to each other.

A stiffener or positioner, referred to herein as a pusher catheter 42, extends proximally from the handle assembly 8. The pusher catheter 42 has a proximal end 44, a distal end 46, and a lumen extending therebetween, and is coaxial with the inner cannula 24. The distal end 46 of the pusher catheter 42 may be coupled to the stationary gripping portion 10, where it extends proximally through and beyond the proximal gripping portion 12 towards the stent graft retention region 20.

In FIG. 3, the stationary gripping portion 10 includes an irrigation port 40. This irrigation port 40 provides fluid communication with the pusher catheter 42 lumen. The pusher catheter 42 may be retained within the stationary gripping portion 10 by various means, including threaded attachment, adhesives, welding, and/or other suitable attachment mechanisms. As shown in FIG. 3, the distal end 46 of the pusher catheter 42 may terminate within the housing provided by the stationary gripping portion 10. A ring like component 90 disposed about a distal end 46 of the pusher catheter 42 may serve to anchor, stabilize and position the distal end 46 of the pusher catheter 42 within the interior of the housing provided by the stationary gripping portion 10. Additional stiffening materials or components, for example, a stiffening rod, (not shown) may be disposed over or used in combination with the inner cannula 24 and/or the pusher catheter 42 for additional stability and maneuverability when the delivery device 2 is in use.

The pusher catheter 42 may be constructed from various materials. In one example, a proximal portion of the pusher catheter 42 introduced into a patient may comprise a polymer, sometimes referred to as VRDT (or vinyl radiopaque dilator tubing), plastics, metals, alloys or a combination thereof. A distal portion of the pusher catheter 42 may comprise the same material as the proximal portion of the pusher catheter 42 or may be a different material, including but not limited to, plastics, polymers, alloys, metals or a combination thereof, that provide sufficient maneuverability and stiffness to the pusher catheter 42 as necessary and desired.

As shown generally in FIG. 2, the sheath 28 has a proximal end 30, a distal end 32, and a lumen extending therebetween. In a pre-deployment configuration, the sheath 28 is configured to cover and assist in retaining a prosthesis, such as a stent graft 56, in a radially inwardly compressed, low-profile configuration during delivery of the prosthesis to a target site within a patient's anatomy.

The sheath 28 extends proximally from the proximal end of the proximal gripping portion 12 to the nose cone dilator 22 at the proximal end 4 of the delivery device 2. The distal end 32 of the sheath 28 may be secured to the proximal end 48 of the proximal gripping portion 12 by a friction fit, threaded engagement, adhesives, or other attachment mechanisms or combinations thereof. Due to the coupling between the proximal gripping portion 12 and the sheath 28, distal longitudinal movement of the proximal gripping portion 12 retracts the sheath 28 distally along the longitudinal axis 34 when the proximal gripping portion 12 is retracted distally along the rails 14, 16, 18 during deployment. Upon retraction of the proximal gripping portion 12, the sheath 28 is retracted to uncover the stent graft 56 from a proximal to distal direction during deployment. Once uncovered, the stent graft 56 can be deployed by retraction and removal of the one or more trigger wires that retain the stent graft 56 upon the inner cannula 24 at the stent graft retention region 20, as described herein.

As generally shown in FIG. 1, a rail assembly 13 extends distally from the proximal gripping portion 12, such that the rail assembly extends between the stationary gripping portion 10 and the proximal gripping portion 12 along a longitudinal axis 34 in a pre-deployment configuration. The rail assembly 13 is configured to reduce and/or prevent independent axial rotation of the proximal gripping portion 12 about the longitudinal axis 34 relative to the stationary gripping portion 10. The rail assembly 13 is also configured to reduce and/or prevent independent axial rotation of the handle assembly 8 about the longitudinal axis 34 relative to a prosthesis located at the proximal end 4 of the delivery device 2. As such, the rail assembly 13 substantially reduces and/or prevents the accumulation of torque along the length of the delivery device 2, between the components of the handle assembly 8, and also along the length of the delivery device 2 between the handle assembly 8 and the nose cone dilator 22.

In some embodiments, the rail assembly 13 is configured to facilitate a substantially 1:1 ratio of axial rotation between the handle assembly 8 and the prosthesis. In other words, a particular degree of rotation of the handle assembly 8, such as by rotation of the physician's wrist during use to properly position a prosthesis during a procedure, may result in the same degree of rotation of the prosthesis within the vessel lumen. This provides precise control over positioning and placement of the prosthesis during a procedure. Furthermore, when a physician grasps the stationary gripping portion 10 and rotates his wrist to position the prosthesis at the proximal end of the delivery device 2 prior to sheath retraction, the rail assembly 13 serves as a stabilizing and reinforcing coupling between the stationary gripping portion 10 and the proximal gripping portion 12. As such, the rail assembly 13 substantially reduces and/or prevents the accumulation of torque between the stationary gripping portion 10 and the proximal gripping portion 12. This also provides precise control over positioning and placement of the prosthesis while also serving to prevent twisting or torque build up along the length of the inner cannula 24, the sheath 28 and/or a pusher catheter 42.

In one example, the rail assembly 13 may comprise a single rail 14. However, as shown in the embodiment in FIG. 1, the rail assembly 13 may include a first rail 14, a second rail 16 and a third rail 18, although more rails may be included as part of the rail assembly 13 as necessary or desired. Reference herein to a handle assembly 8 comprising one rail 14 may apply to handle assembly 8 embodiments with more than one rail.

The longitudinal axis 34 is at least substantially parallel to the rails 14, 16, 18. The rails 14, 16, 18 in FIG. 1 are arranged about, and parallel to, the longitudinal axis 34. The rails 14, 16, 18 are also parallel to each other and each rail is spaced apart from the other rails. The rails 14, 16, 18 may be spaced apart from each other to provide physical and visual access to the space formed inside of and defined by an inner surface of the rails 14, 16, 18 that faces the longitudinal axis. The space and/or distance between each of the respective rails 14, 16 and 18 may be the same or it may be different.

Figures 4, 5:
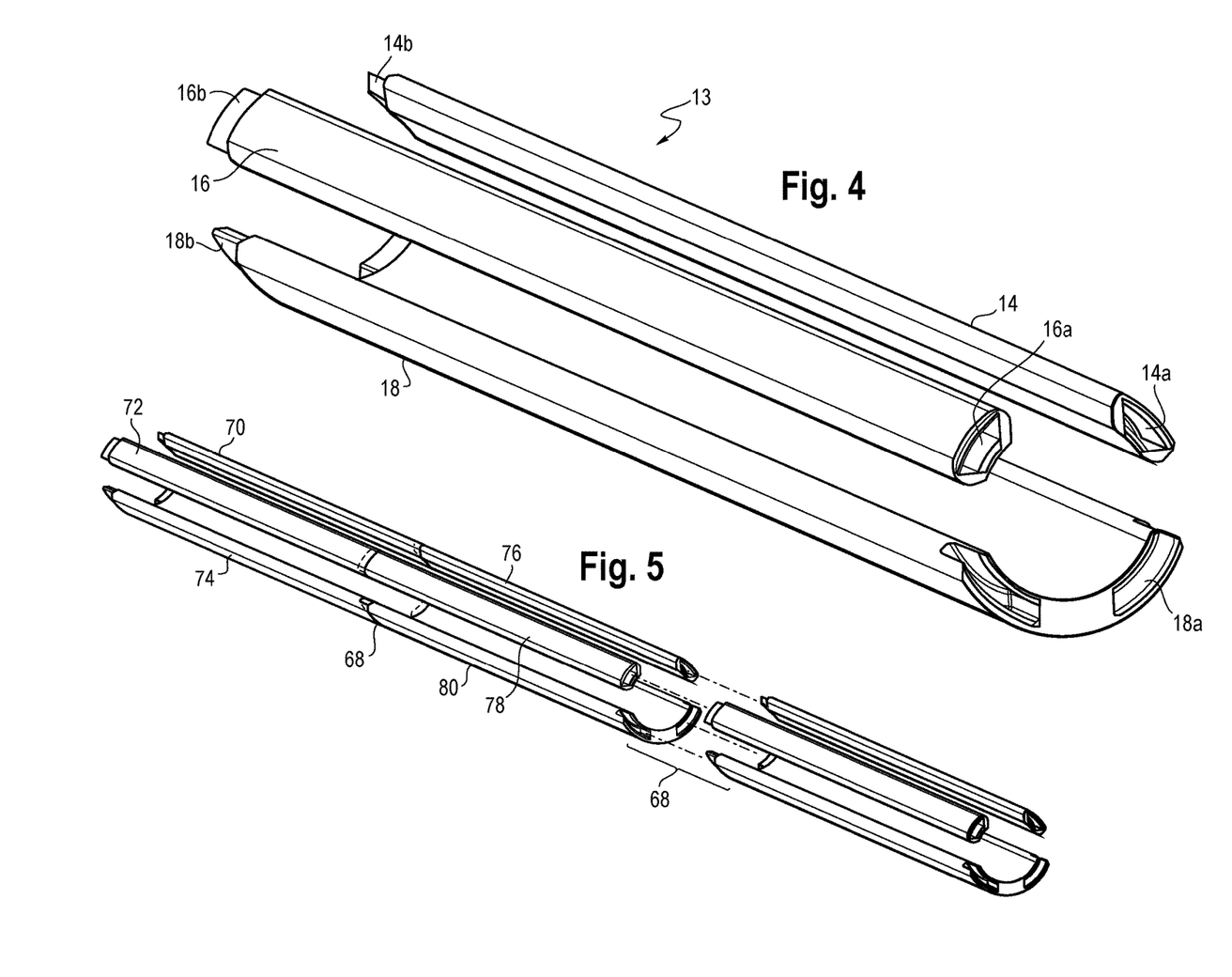
FIG. 4 is a perspective view of a rail assembly comprising a first rail, a second rail, and a third rail, each having a male portion and a female portion.
FIG. 5 is an exploded perspective view of the rail assembly of FIG. 4 connected to two additional rail assemblies, where at each separable joint, a male end of a rail couples with a female end of another rail.

The rail assembly 13, as shown in FIGS. 1 and 4, may be a variety of shapes, sizes, widths, and lengths. In one embodiment, two rails 14, 16 have substantially the same configuration, dimensions and shape. A third rail 18 may be the same length as each of the first two rails 14, 16, but, in one embodiment, the width of the third rail 18 has a greater width than the first two rails 14, 16. Each rail 14, 16, 18 may be slightly curved along its width such that each of the rails that make up the rail assembly 13 are generally disposed about, and curve around, the longitudinal axis 34. The degree of curvature of each rail 14, 16 and 18 may be the same or it may be different.

In one example, each of the rails 14, 16, 18 has a female end 14a, 16a, 18a respectively, and a male end 14b, 16b, 18b, respectively, as shown in FIG. 4. The female ends 14a, 16a, 18a may include one or more recesses or openings while the male ends 14b, 16b, 18b may have one or more correspondingly shaped projections. In one example, the first two rails 14, 16 each have a male end 14b, 16b that includes one projection and a female end 14a, 16a that includes one recess. The third rail 18 has a male end 18b that includes two projections and a female end 18a that includes two recesses. The male ends 14b, 16b, 18b and female ends 14a, 16a, 18a of the rails 14, 16, 18 are generally configured to attach the respective ends of the rail assembly 13 to other components of the handle assembly 8. Further detail of an embodiment of the rail assembly 13 is shown in FIG. 4. The female recess 14a, 16a, 18a is shown as having four walls, creating an elongated rectangular or trapezoidal shape, although the recesses may be formed of any suitable shape or dimension. The first rail 14 and second rail 16 and third rail 18 also each have at least one male protrusion. This protrusion corresponds to the shape of the recess of the first and second and third rails 14, 16, 18 so as to provide an interlocking fit between the male protrusion and the female recess of an additional rail assembly to extend the overall length of the rails of the handle assembly 8. The female recesses and male protrusions may also be used to attach or couple the rail assembly to other components of the handle assembly, such as the proximal gripping portion 12 and/or the end cap 26. While various embodiments for the male and female ends of the rail assembly 13 have been described herein, it will be apparent to those of ordinary skill in the art that many more examples, embodiments, and implementations are possible within the scope of the claims to allow for the rails to be attached to additional rails to extend the length of the rails or, in other embodiments, to allow for the overall length of the rails to be shortened and/or coupled to other components of the handle assembly 8. For example, it is also contemplated that other methods or mechanisms of attachment may be used as an alternative to, or in addition to, the male and female configurations presently shown to attach one or more ends of the rail assembly 13 to other component(s) of the handle assembly 8.

Figures 6, 7, 8:
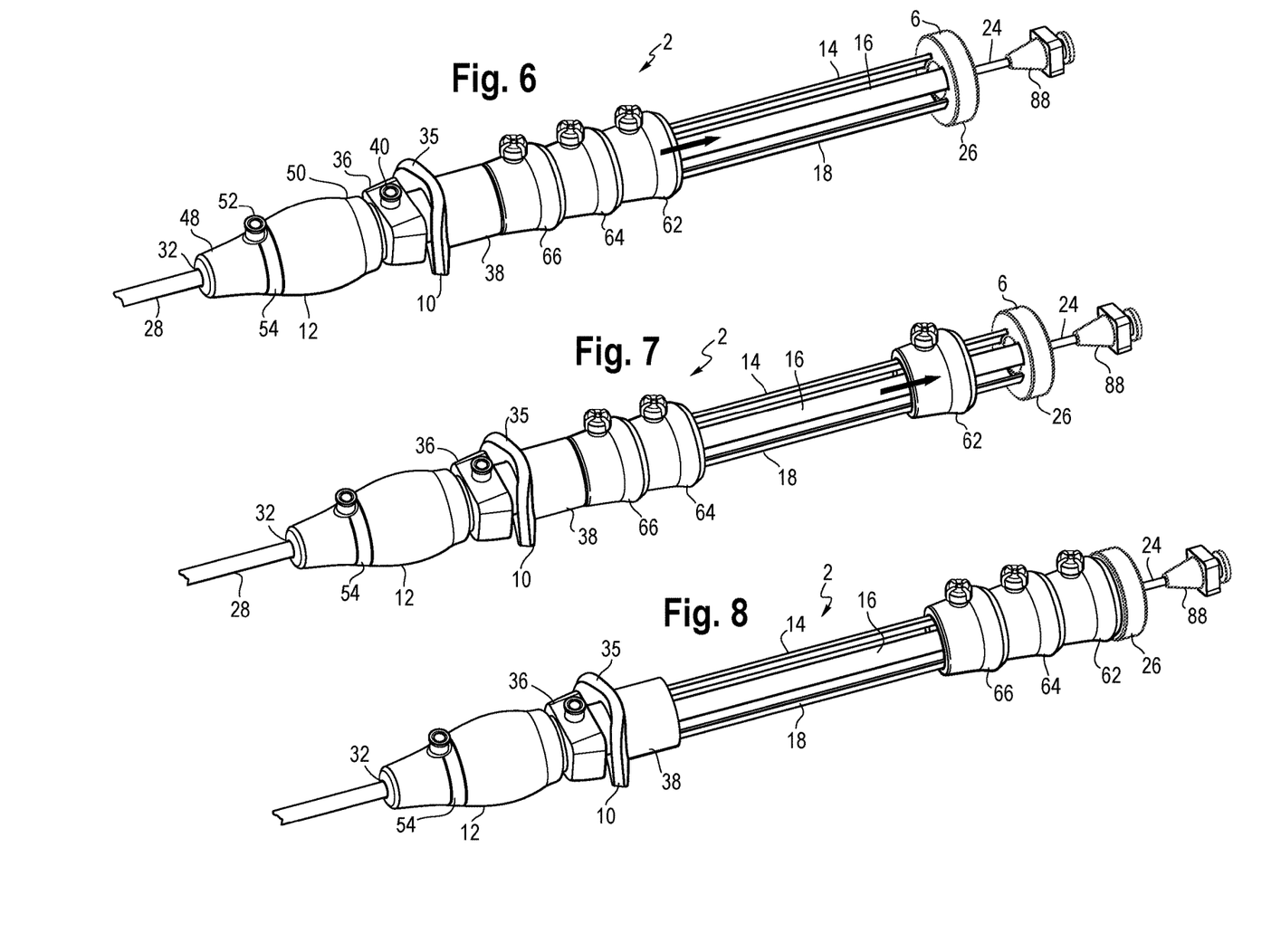
FIG. 6 is a side perspective view of an example of a handle assembly in a configuration after sheath retraction and before trigger wire release.
FIG. 7 is a side perspective view of an example of a handle assembly with the distal-most trigger wire release mechanism sliding distally upon the rail assembly, to deploy at least a portion of the prosthesis.
FIG. 8 is a side perspective view of an example of a handle assembly after all three trigger wire release mechanisms have been moved distally upon the rail assembly to deploy the prosthesis.

In one example, as shown in FIG. 1, the proximal end of the rail assembly 13 is attached, secured and/or coupled to a proximal gripping portion 12. Further, the distal end of the rail assembly 13 may be attached, secured and/or coupled to a distal most structure, such as an end cap 26 as shown in FIG. 6.

In one example, as shown in FIGS. 1 and 6-8, a stationary gripping portion 10 is disposed about the rails 14, 16, 18 at a location between a proximal gripping portion 12 and the distal-most end of the handle assembly 8, such as, for example, the end cap 26. In one example, the stationary gripping portion 10 has a proximal end 36 and a distal end 38. The rails 14, 16, 18 extend through at least a portion of the stationary gripping portion 10. During use, each of the rails 14, 16, 18 is longitudinally moveable relative to the stationary gripping portion 10 while the stationary gripping portion 10 remains in a fixed location in space. The rails 14, 16, 18 are shown in FIG. 1 in a position extending distally from the proximal gripping portion 12, through the stationary gripping portion 10, to the end cap 26.

The stationary gripping portion 10 may comprise an ergonomic shape for the user to grasp securely and comfortably during use of the device. In one example, the stationary gripping portion 10 may include one or more projections or ribs comprised of soft or semi-soft rubber, plastic and/or other materials that provide a comfortable and secure gripping surface. In FIG. 1, the stationary gripping portion 10 includes a radially-outwardly extending portion, or flange 35. The flange 35 extends radially outward from the longitudinal axis 34. This flange 35 in FIG. 1 has a rectangular shape, but flange 35 may be formed as a variety of different shapes and sizes as long as the stationary gripping portion 10 is suitable for holding by a user. The stationary gripping portion 10 may also provide a housing for other components. For example, as shown in FIGS. 1 and 3, the stationary gripping portion 10 may include a fluid port 40 for introducing fluids to a patient during a procedure, such as through the inner cannula 24 and/or through the pusher catheter 42. Fluids may also be drained or eliminated through the fluid port 40.

The proximal gripping portion 12 has a proximal end 48 and a distal end 50. The proximal gripping portion 12 is moveable along the longitudinal axis 34 and moveable relative to the stationary gripping portion 10. The proximal gripping portion 12 is moveable distally along the longitudinal axis 34 toward the stationary gripping portion 10 during use from a first or proximal position (FIG. 1) to a second or distal position (FIGS. 6-8) where the proximal gripping portion 12 is just proximal to and adjacent to the stationary gripping portion 10. With the proximal gripping portion 12 in this first or proximal position, the device is in a pre-deployment configuration. In this configuration, the device can be introduced into a patient's vasculature and manipulated by the user to a target site for vessel repair and/or for deployment of a prosthesis, such as a stent graft 56. In a pre-deployment configuration, a prosthesis carried at the proximal end of the device is covered by a sheath 28.

The sheath 28 retains or holds the stent graft 56 in a radially-inward collapsed and constricted configuration for ease of introduction and manipulation within the vasculature. When the proximal gripping portion 12 is moved to the second or distal-most position as shown in FIG. 6, the sheath 28 is retracted as the proximal gripping portion is retracted, allowing the stent graft 56 retained at the proximal end 4 of the device 2 to be uncovered and subsequently deployed.

For example, once the sheath 28 has been retracted to uncover the stent graft 56, deployment of the stent graft 56 may occur in one or more consecutive sequential steps, such as by the removal of one or more trigger wires, release of one or more diameter reducing ties or other mechanisms that retain the stent graft 56 on the delivery device 2. In one non-limiting example, it may be desirable to deploy one end of the stent graft 56 prior to deployment of other parts of the stent graft 56. The proximal end 58 of the stent graft 56 may be deployed first, followed by deployment or release of other diameter-reducing ties at one or more points along the length of the stent graft 56 followed by deployment of the distal end 60 of the stent graft 56. It is also contemplated that deployment of the stent graft 56 can occur in a different sequence or by other mechanisms upon retraction of the sheath 28.

The proximal gripping portion 12 comprises a proximal end 48 and a distal end 50 with an outer surface or side wall extending therebetween to form a housing having an interior. As shown in FIG. 3, a haemostatic valve 54 may be housed within the interior of the proximal gripping portion 12. In one example, as shown in FIG. 3, the haemostatic valve 54 prevents the backflow of fluid within the delivery device 2. This includes any fluids introduced prior to a procedure to flush the device and/or fluid, including blood, from flowing back into the device during a procedure. The proximal gripping portion 12 may house additional mechanical components. As shown in FIG. 3, the proximal gripping portion 12 may also include an irrigation port 52. This irrigation port 52 provides fluid communication with the sheath 28 lumen and/or the lumen of the pusher catheter 42 and/or the inner cannula 24. In one example, the irrigation port 52 extending through the housing of the proximal gripping portion 12 may also be referred to as a sheath flush port. The irrigation port 52 may include a one way valve that communicates with the sheath lumen to allow flushing of the sheath 28 prior to introduction into the vasculature.

At the distal end of the rail assembly 13 is an end cap 26 shaped as disk or ring. The male portion of each rail 14b, 16b, 18b extends to and/or through the end cap 26. The end cap 26 may serve as a stopping point for an object capable of sliding along one or more of the rails 14, 16, 18 including, for example, one or more trigger wire release knobs 62, 64 and/or 66 as described in further detail below. The disk-like shape of the end cap 26 is not intended to be limiting, and a variety of projection shapes and sizes may be suitable.

The handle assembly 8 may include at least one stent graft release mechanism. In one non-limiting example, the stent graft release mechanism may include one or more trigger wire release mechanisms as needed for the sequential deployment of a stent graft 56. While a plurality of trigger wire release mechanisms are shown and described herein for the sequential deployment of a stent graft 56, it will be appreciated that a variety of other methods and mechanisms may be suitable for use with the delivery device 2 to deploy a prosthesis.

An example of one suitable trigger wire release mechanism includes one or more trigger wire release knobs 62, 64, 66 as shown in FIG. 6. A distal end of a trigger wire may be connected, attached or otherwise coupled to a trigger wire release knob. The trigger wire may extend proximally from the trigger wire release knob to a prosthesis carried at the proximal end of the device. The trigger wire may be coupled to the stent graft itself and/or to a diameter reducing tie or other mechanism that holds the stent graft 56 in a radially-inwardly constricted configuration prior to deployment. When the trigger wire is removed or withdrawn, the stent graft is released, (and/or the diameter reducing tie is released), allowing that portion or segment of the stent graft 56 to expand radially-outwardly and deploy. More than one trigger wire may be provided to allow the stent graft 56 to be deployed in stages and in a particular sequence.

As shown in FIGS. 6-8, 10, and 11, at least three trigger wires are provided. The proximal end of each trigger wire communicates with the stent graft and/or with one or more diameter reducing ties disposed about a portion of the prosthesis, while the distal end of each trigger wire communicates with a separate trigger wire release knob located on the handle assembly 8. The distal-most trigger wire release knob 62 is coupled to a trigger wire that may communicate with the proximal end of the stent graft 56 and therefore controls the release and deployment of the proximal end 58 of the stent graft 56. The middle trigger wire release knob 64 is coupled to another trigger wire that may communicate with the stent graft and/or a diameter reducing tie located along the length of the stent graft 56, thus controlling the release and deployment of a central segment of the stent graft 56. The proximal-most trigger wire release knob 66 is coupled to a third trigger wire that may communicate with the distal-most end of the stent graft 56 and therefore controls the release and deployment of the distal end 60 of the stent graft 56. More or fewer trigger wire release knobs may be provided as necessary and desired depending on the number of trigger wires provided. An additional trigger wire release knob may be provided for each trigger wire, such that in FIGS. 6-8, 10, and 11, three trigger wires are present, with each trigger wire being attached to one of the trigger wire release knobs 62, 64, 66 at its distal end and attached at its proximal end to a particular portion of the stent graft and/or to a release mechanism disposed on the stent graft 56 (e.g. a specific diameter reducing tie).

For example, FIG. 1 and FIGS. 6-8 show a non-limiting example of a release mechanism that can be operated using handle assembly 8. The release mechanism includes three trigger wire release knobs 62, 64, 66. As shown in FIG. 1, each trigger wire release knob 62, 64, 66 is slidably disposed over the rails 14, 16, 18. One or more trigger wire(s) extend proximally from each trigger wire release knob 62, 64, 66 to one or more portions of the stent-graft. The distal end of the trigger wire(s) may be secured to, connected or otherwise attached to a trigger wire release knob by one or more screws, or another attachment mechanism including adhesives, welding, crimping, or a combination thereof.

The trigger wire release knobs 62, 64, 66 have a range of longitudinal movement upon the rails 14, 16, 18 depending on several factors including, but not limited to, the length of the rail assembly 13 and/or the position of the proximal gripping portion 12. In FIG. 1, which generally represents a pre-deployment configuration, the proximal gripping portion 12 is spaced proximally from the stationary gripping portion 10 by a pre-selected distance. This pre-selected distance may correspond generally to the length of the stent graft 56 located at the proximal end of the device, such that distal longitudinal movement of the proximal gripping portion 12 towards the stationary gripping portion 10 provides adequate distance/length to retract the sheath 28 and fully uncover the stent graft 56 as described below.

The sheath 28 extends proximally from the proximal gripping portion 12 to the proximal end 4 of the delivery device 2 where it is disposed about stent graft 56. In this pre-deployment configuration, the rail assembly 13 extends between the stationary gripping portion 10 and the proximal gripping portion 12. In this position, the end cap 26 abuts the distal-most trigger wire release knob 62, such that all three of the trigger wire release knobs 62, 64, 66 are captured snugly between the end cap 26 and the distal end 38 of the stationary gripping portion 10. This prevents premature and unintended longitudinal movement of the trigger wire release knobs 62, 64, 66, thereby preventing premature release of the trigger wire(s) from the stent graft 56. Longitudinal movement of the proximal gripping portion 12 in the distal direction towards the stationary gripping portion 10 pulls the rails 14, 16, 18 longitudinally through the stationary gripping portion 10. As the proximal gripping portion 12 is pulled distally towards the stationary gripping portion 10, the sheath 28 is also retracted distally to uncover at least a portion of the stent graft 56 at the proximal end of the device. The end cap 26 attached to the distal ends of the rails 14, 16, 18 moves distally along with the rails 14, 16, 18.

As shown in FIG. 6, with the proximal gripping portion 12 moved to its distal-most position and abutting the proximal end of the stationary gripping portion 10, the rails 14, 16, 18 extend distally (e.g. rearwardly) from the stationary gripping portion 10. In this position, there is now a length of the rails 14, 16, 18 available for the trigger wire release knobs 62, 64, 66 to slide distally upon when the user is ready to retract and release the trigger wire(s) to sequentially deploy the graft. In other words, a length of the rails 14, 16, 18 becomes available and longitudinal movement of the trigger wire release knobs 62, 64, 66 upon the rail assembly 13 becomes available to release the stent graft 56 during deployment.

Figure 9:
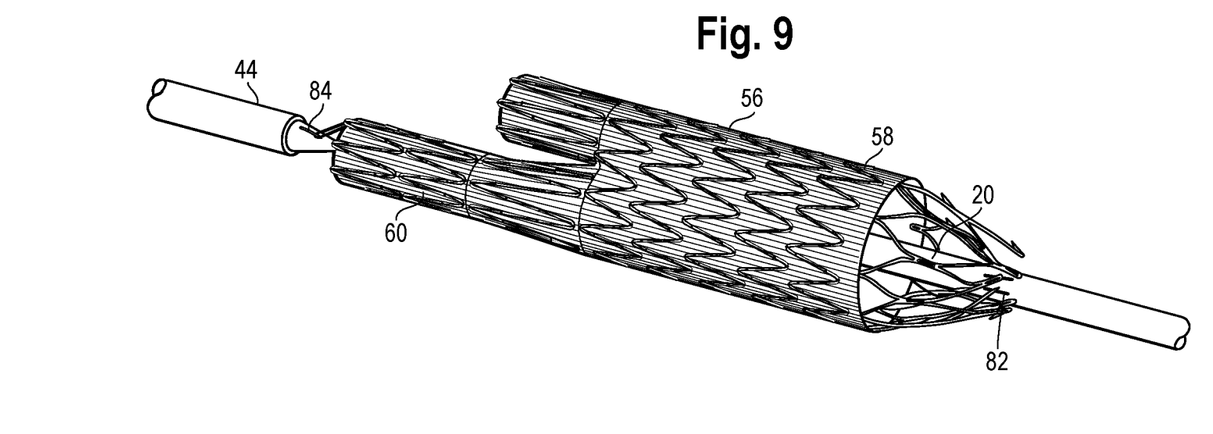
FIG. 9 is a side perspective view of a stent graft attached to the proximal end of an inner cannula by a proximal trigger wire attachment and a distal trigger wire attachment.
Figure 10:
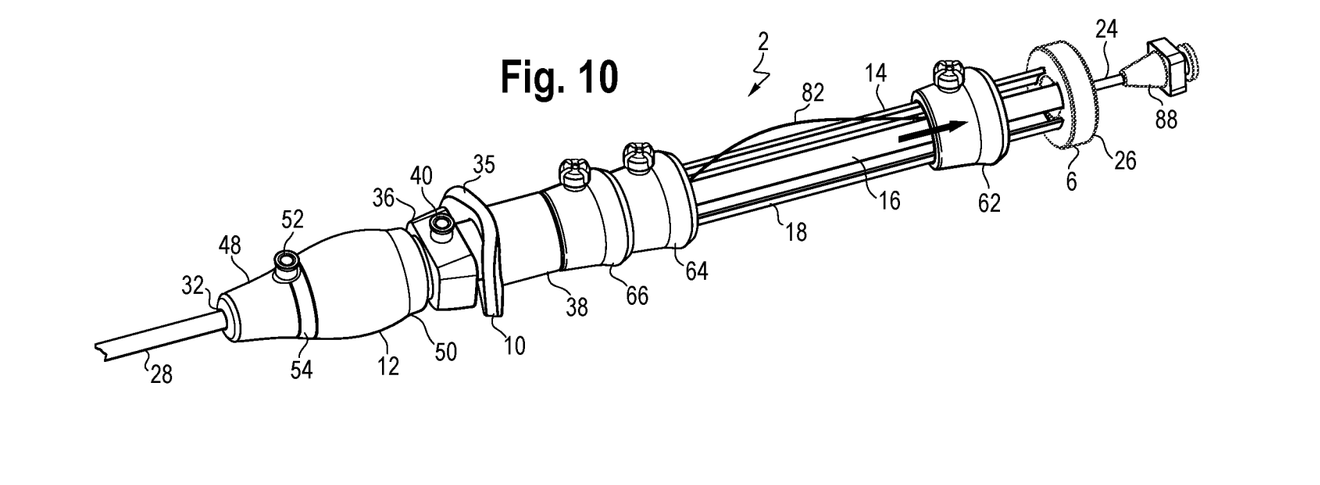
FIG. 10 is a perspective view of an example of a handle assembly and the distal-most trigger wire release mechanism sliding distally along the rail assembly to retract and release a first trigger wire.

In embodiments where there is more than one trigger wire release knob, the multiple trigger wire release knobs 62, 64, 66 are sequentially moveable to deploy the stent graft 56. As an example, after the sheath 28 has been at least partially retracted by sliding the proximal gripping portion 12 distally to a position as shown in FIG. 6 to expose at least a portion of the stent graft 56, the user can then manipulate the trigger wire release knob(s) 62, 64, 66 individually to deploy the stent graft 56. In one example, the user can slide the first trigger wire release knob 62 distally along the length of rails 14, 16, 18, until the first trigger wire release knob 62 abuts the end cap 26 as shown in FIG. 7. Distal longitudinal movement of the first trigger wire release knob 62 serves to distally pull or retract one or more trigger wires attached to it. As such, when the first trigger wire release knob 62 is retracted along the rails 14, 16, 18, from a position as shown in FIG. 6 to the distal position shown in FIG. 7, the trigger wire(s) 82 attached to the first trigger wire release knob 62 (also shown in FIG. 10) are pulled rearwardly and removed from the stent graft 56. In one example, the retraction of the first trigger wire release knob 62 serves to remove one or more trigger wires 82 attached to the proximal end 58 of the stent graft 56 to allow deployment of the proximal end 58 of the stent graft 56. One non-limiting example of the attachment of trigger wire 82 to the proximal end 58 of the stent graft 56 is shown in FIG. 9.

The second trigger wire release knob 64 is not capable of any distal longitudinal movement upon the rails 14, 16, 18 until the first trigger wire release knob 62 is moved distally, because the second trigger wire release knob 64 is sandwiched between the first trigger wire release knob 62 and the third trigger wire release knob 66. For this reason, the trigger wire(s) operatively connected to the second trigger wire release knob 64 are prevented from being inadvertently and/or prematurely removed from the stent graft 56 before deployment of the proximal end 58 of the stent graft 56 as described above. Only after the first trigger wire release knob 62 has been retracted to deploy the proximal end 58 of the stent graft 56, can the user longitudinally retract the second trigger wire release knob 64 by sliding it distally along the rails 14, 16, 18.

Distal longitudinal movement of the second trigger wire release knob 64 along the rails 14, 16, 18, can proceed, until the second trigger wire release knob 64 abuts the first trigger wire release knob 62 or another predetermined stopping point. As the second trigger wire release knob 64 is moved longitudinally along the rails 14, 16, 18 in a distal direction, the trigger wire(s) 84 attached to or otherwise operatively connected to the second trigger wire release knob 64 is pulled back with the knob 64 in a distal direction, thus removing the trigger wire(s) 84 from distal end 60 of the stent graft 56. This allows the distal end 60 of the stent graft 56 to expand and deploy. One non-limiting example of attachment of trigger wire 84 to the distal end 60 of the stent graft 56 is shown in FIG. 9.

The third trigger wire release knob 66 is not capable of distal longitudinal movement upon the rails 14, 16, 18 until the second trigger wire release knob 64 is retracted, because the third trigger wire release knob 66 is sandwiched between the second trigger wire release knob 64 and the stationary gripping portion 10. For this reason, the trigger wire(s) operatively connected to the third trigger wire release knob 66 (shown in FIG. 11) are prevented from being inadvertently and/or prematurely removed from the stent graft 56 before deployment of the distal end 60 of the stent graft 56 as described above. Only after the second trigger wire release knob 64 has been retracted to deploy the distal end of the stent graft 56, can the user longitudinally retract the third trigger wire release knob 66 by sliding it distally along the rails 14, 16, 18.

Figure 11:
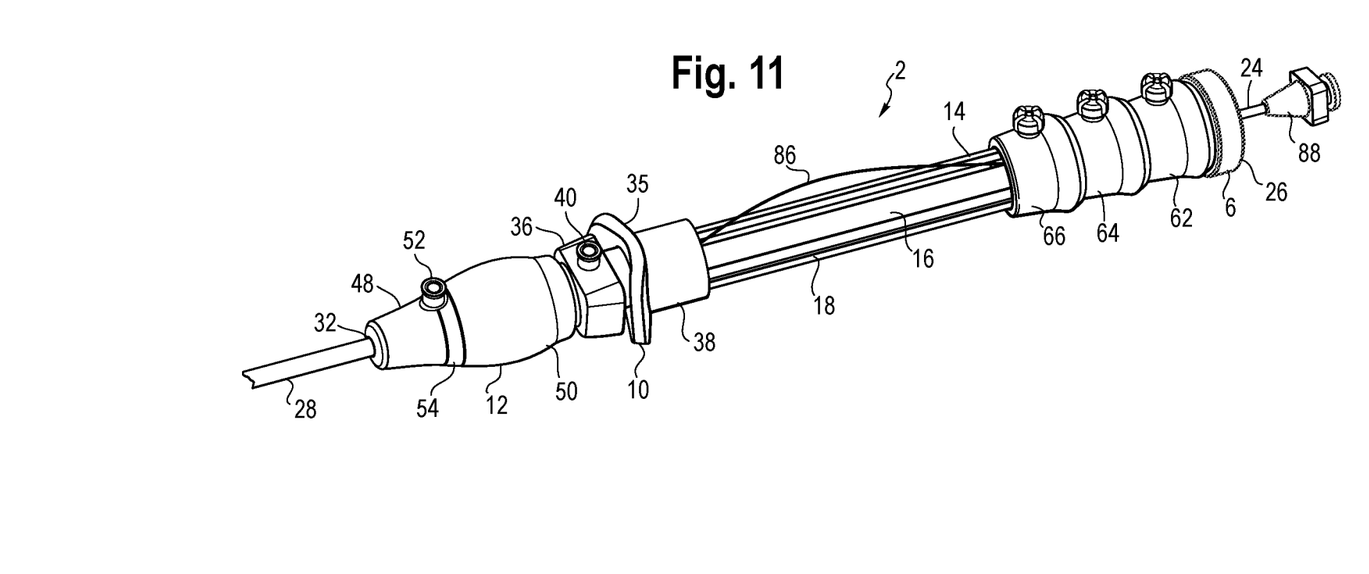
FIG. 11 is a perspective view of an example of a handle assembly having all three trigger wire release mechanisms moved distally along the rail assembly to retract and release a third trigger wire.

After the second trigger wire release knob 64 has been retracted and deployment of the distal end 60 of the stent graft 56 is complete, the user can then manipulate the third trigger wire release knob 66 by sliding the third trigger wire release knob 66 longitudinally along the rails 14, 16, 18 in a distal direction until the third trigger wire release knob 66 abuts the second trigger wire release knob 64 or another predetermined stopping point as shown in FIG. 8 and FIG. 11.

This length of the rails 14, 16, 18, and thus, the longitudinal distance available upon which the trigger wire release knobs 62, 64, 66 can be distally retracted, is modifiable to suit a particular procedure, a particular stent graft size and/or length as well as the length of the one or more trigger wires.

In some embodiments, as shown generally in FIGS. 2 and 4, the female ends 14a, 16a, 18a of the rail assembly 13 are located at the proximal end of each rail 14, 16, 18 and male ends 14b, 16b, 18b are located at the distal end of each rail 14, 16, 18. As shown in FIG. 2, the female rail ends 14a, 16a, 18a are coupled to the proximal gripping portion 12 which houses the haemostatic valve 54. In some embodiments, the rails 14, 16, 18 may be coupled to the proximal gripping portion 12 by various attachment mechanisms, including but not limited to friction fit, adhesives and/or bonding.

Each of the rails 14, 16, 18 is connectable to another rail, end to end, to extend the longitudinal length of the rail assembly 13 as necessary or desired. In one example, the connection is facilitated by the interlocking capability of a male end of one rail with a female end of another rail. In this manner, a plurality of rails may be used to extend overall rail length of the handle assembly 8. FIG. 2 shows rails 14, 16, 18 being attached to additional rails with an example of the relative position of the end cap 26 in multiple positions that corresponds to a particular selected rail length. A variety of rail lengths may be used in combination to provide customizable options for a user. For example, additional rails may be used to extend the overall rail length to accommodate a larger and/or longer stent graft, allow for further longitudinal movement of the trigger wire release knobs 62, 64, 66 in a distal direction during deployment and/or other reasons when a longer handle assembly 8 is desirable or necessary depending on the particular procedure being performed. Characteristics of rails 14, 16, 18 described herein also apply to extension rails, for example 70, 72, 74, 76, 78, 80, shown in FIG. 2.

In some examples, the rails 14, 16, 18 include at least one predetermined breaking point 68. The predetermined breaking point 68 allows a user to detach at least a portion of a rail from the delivery device 2 before, during, or after a procedure. A predetermined breaking point 68 may be a weakened rail portion or, as shown in FIG. 5, a separable rail joint. A separable rail joint may be formed by the connection of a male end of one rail with a female end of another rail. In one example, the rails may be initially produced and assembled to accommodate relatively larger stent grafts or other prosthesis or to accommodate standard off-the-shelf prostheses. The rails can be broken apart at the predetermined breaking point 68 (or points) if the stent graft or other prosthesis ultimately used with the delivery device 2 is shorter. The male attachment of the shortened rails can be attached to the end cap 26, and the female end coupled to the proximal gripping portion 12 or other portions or components of the handle assembly 8 as described above.

Further detail of an embodiment of rails 14, 16, 18 coupled to extension rails 70, 72, 74, 76, 78, 80 is shown in FIG. 5. Extension rails are shown coupled at corresponding male projections to female recesses. The dotted lines extending between rails 14, 16, 18 and extension rails 70, 72, 74, 76, 78, 80 demonstrate the interlocking capability of the male ends of the rails with female recesses of extension rails 70, 72, 74, 76, 78, 80, which may also provide a breaking point to break apart and/or otherwise shorten the overall length of the rails. The addition of extension rails 70, 72, 74, 76, 78, 80 is at the discretion of the user of the delivery device 2. Modifications to the overall length of rails, including connected rails, may be done before, during, or after a procedure. In FIG. 5, each rail 14, 16, 18 and extension rails 70, 72, 74, 76, 78, 80 are the same length. However, extension rails 70, 72, 74, 76, 78, 80 may have different lengths.

FIGS. 1, 6, 7, and 8 show multiple configurations of a handle assembly 8 at various stages of use. The various steps of use, including delivery and deployment of a prosthesis using the handle assembly 8, will now be described. FIG. 1 illustrates the handle assembly 8 in a pre-deployment configuration. The proximal gripping portion 12 is in its proximal-most position, such that the sheath 28 extends proximally from the proximal gripping portion 12 and is covering a stent graft 56 or other prosthesis carried on the inner cannula 24 at the proximal end 4 of the delivery device 2. FIG. 6 illustrates the handle assembly 8 of FIG. 1 with the proximal gripping portion 12 retracted longitudinally in a distal direction to retract the sheath 28. As the proximal gripping portion 12 is retracted distally to retract the sheath 28, the stent graft 56 is uncovered from a proximal to distal direction. Also, as the proximal gripping portion 12 is retracted distally, the rail assembly 13 moves distally with it.

More specifically, as shown in FIG. 6, the rails 14, 16, 18 extend distally behind the stationary gripping portion 10 due to movement in a distal direction of the proximal gripping portion 12 from the position shown in FIG. 1 to the position shown in FIG. 6, as the user applies force to the proximal gripping portion 12 while holding the stationary gripping portion 10 in a stationary position in space. Movement of the proximal gripping portion 12 in the distal direction along the longitudinal axis 34 pulled the rails 14, 16, 18 distally due to the attachment of the rails 14, 16, 18 to the proximal gripping portion 12. Distal movement of the rails 14, 16, 18 pulled by the proximal gripping portion 12 causing the rails 14, 16, 18 to slide through the stationary gripping portion 10.

Thus, when the proximal gripping portion 12 is in its distal-most position, adjacent to and/or abutting the stationary gripping portion 10 as shown in FIG. 6, the rails 14, 16, 18 extend in their fully extended position and distally behind the stationary gripping portion 10 and trigger wire release knobs 62, 64, 66. In this position, the rails 14, 16, 18 provide a longitudinal length upon which the trigger wire release knobs 62, 64, 66 may now slide during deployment. In other words, as each of the trigger wire release knobs 62, 64, 66 are moved distally upon the rails 14, 16, 18 in a sequential manner, the one or more trigger wires coupled to each of the trigger wire release knobs 62, 64, 66 are also retracted and release from the stent graft 56 at the proximal end of the device. This sequential removal of trigger wires permits the user to deploy the stent graft 56 in a controlled, sequential manner during deployment of the stent graft 56.

With the rails 14, 16, 18 fully extended in a distal direction behind the stationary gripping portion 10, the first trigger wire release knob 62, which is the distal-most knob, can be moved distally as shown by the arrow in FIG. 6. A user moves the first trigger wire release knob 62 by sliding the first trigger wire release knob 62 from the starting point shown in FIG. 6 (where the first knob 62 is disposed over the rails 14, 16, 18 and adjacent to the second trigger wire release knob 64) over the surface of the rails 14, 16, 18 and towards the distal end of the rails 14, 16, 18. The first trigger wire release knob 62 shown in FIG. 6 is capable of being moved further distally along the rails 14, 16, 18 until the distal end of the first trigger wire release knob 62 abuts the end cap 26 as shown in FIG. 7.

This same process continues, as the user is then permitted to slide the second trigger wire release knob 64 distally along the rails 14, 16, 18, until the distal end of the second trigger wire release knob 64 abuts the first trigger wire release knob 62. With the second trigger wire release knob 64 in a distal most position, the third trigger wire release knob 66 can then be moved distally upon and along the rails 14, 16, 18, until the distal end of the third trigger wire release knob 66 abuts the second trigger wire release knob 64. Where more trigger release knobs are present, this process can continue until all trigger wire release knobs have been manipulated by the user to fully deploy the stent graft 56.

FIG. 8 illustrates the three trigger wire release knobs 62, 64, 66 after they have been moved in a distal direction upon the outer surface of the rails 14, 16, 18 with respect to their position in FIG. 6.

During a procedure, the user may need to rotate the handle assembly 8 to adjust the position of a prosthesis within a vessel lumen. The handle assembly 8 may be rotated for example, such as by rotation of the user's wrist. Because the rails 14, 16, 18 couple the proximal gripping portion 12 to the stationary gripping portion 10, axial rotation of any portion of the handle assembly 8, such as the proximal gripping portion 12, ensures that the rotation of the remaining components of the handle assembly 8, such as the stationary gripping portion 10 is substantially the same as the axial rotation of the proximal gripping portion 12. In other words, substantially the same amount of torque applied to the stationary gripping portion 10 is transferred to the proximal gripping portion 12 by the rails 14, 16, 18. Also, conversely, substantially the same amount of torque applied to the proximal gripping portion 12 is transferred to the stationary gripping portion 10 by the rails 14, 16, 18.

Similarly, because the inner cannula 24 is disposed through the handle assembly 8 and the rails 14, 16, 18 couple the proximal gripping portion 12 to the stationary gripping portion 10, axial rotation of any portion of the handle assembly 8, such as the proximal gripping portion 12, ensures that the rotation of the inner cannula 24 and stent graft 56 disposed on the stent graft retention region 20 of the inner cannula 24 is substantially the same as axial rotation of the handle assembly 8. In other words, substantially the same amount of torque applied to the proximal gripping portion 12 or the stationary gripping portion 10 of the handle assembly 8 is transferred to the inner cannula 24 to prevent twisting and/or the build up of torque along the length of the delivery device 2.

When deployment of a stent graft 56 is desired, removal of the trigger wires from the stent graft 56, accomplished by distal retraction of the trigger wire release knob(s) 62, 64, 66 allows the stent graft 56 to move from a radially-inwardly constrained delivery configuration to a radially-outwardly expanded configuration within a vessel. The trigger wire release knobs 62, 64, 66 cannot be retracted in order to release the stent graft 56 from a radially-inwardly constrained delivery configuration to an appropriate state of deployment until after the proximal gripping portion 12 has been retracted to withdraw the sheath 28 and thereby expose the stent graft 56. This is because the rails 14, 16, 18 are not moved to their distal-most position as shown in FIG. 6 until after the proximal gripping portion 12 has been retracted in a distal direction to withdraw the sheath 28, thereby moving the rails 14, 16, 18 distally backward to provide a longitudinal distance or length upon which the trigger wire release knobs 62, 64, 66 can slide distally. In other words, until the proximal gripping portion 12 is retracted distally to withdraw the sheath 28, the trigger wire release knobs 62, 64, 66 are sandwiched between the distal end 38 of the stationary gripping portion 10 and the end cap 26. This structural arrangement prevents premature and unintended release of the trigger wires until the sheath 28 has been retracted to expose the stent graft 56.

The stent graft 56 is coupled to the stent graft retention region 20 of the inner cannula 24 such as by one or more trigger wires and/or circumferential diameter-reducing ties. The coupling releasably secures the stent graft 56 to radially-inwardly restrain the stent graft 56 in a manner that may subsequently facilitate insertion of the proximal end 4 of the delivery device 2 to a target location within a vessel lumen.

In addition to the trigger wires and/or diameter-reducing ties, the sheath 28 is also positioned over the stent graft 56 prior to deployment to radially-inwardly restrain the stent graft 56 for delivery in a low-profile configuration to a target site within a patient's anatomy.

In a non-limiting example of a releasable stent-graft attachment mechanism, three trigger wires (not shown) extend from the handle assembly 8, within the pusher catheter 42, to a stent graft 56 located at the proximal end 4 of the delivery device 2. More particularly, the distal ends of the trigger wires are each coupled to a respective trigger wire release mechanism or knob disposed upon the rails 14, 16, 18 of the handle assembly 8, such as by adhesives, welding, crimping or by set screws. From the trigger wire release knob(s) 62, 64, 66, the trigger wires extend proximally through the lumen of the pusher catheter 42 to the stent graft 56. The trigger wires may be directly or indirectly attached to the stent graft 56, for example, by weaving directly through the graft material or a stent or alternatively by engaging a suture loop. The proximal end of at least one of the trigger wires may be coupled to the proximal end 58 of the stent graft 56 and retained within the distal end of the nose cone dilator 22, such as by friction fit or other suitable attachment means that allow for the trigger wires to be pulled distally and released from the stent graft 56 when deployment of the stent graft 56 is necessary or desired. One or more of the other trigger wires may be coupled to the distal end 60 of the stent graft 56 while another of the trigger wires may be coupled to one or more diameter reducing ties disposed around a center region of the stent graft 56. Other suitable attachment methods or mechanisms may be used to removably attach the trigger wires to the stent graft 56 as would be recognized by one of skill in the art.

The operation of the delivery device 2, and in particular, one non-limiting example of a deployment sequence using a handle assembly 8 of a delivery device 2, will be described below. In this example, use of a delivery device 2 will be described in reference to the implantation of a stent graft 56 in one or more arteries extending distally from the aorta of a patient.

After an incision is made in the artery of the patient, the nose cone dilator 22 is inserted into the incision and the device 2 is tracked over a guide wire (not shown) and advanced to a desired location for placement of the stent graft 56 at the site of an aneurysm or other target site needing repair. A desired imaging modality (i.e., fluoroscopy, MRI, 3D or other imaging techniques) may be used for proper positioning at the target site. Using the desired imaging modality and one or more radiopaque markers (not shown) on the stent graft 56, the user may ensure that the stent graft 56 is properly oriented. A sheath 28 is disposed over the stent graft 56 and extends proximally from the proximal gripping portion 12 up to at least the distal end of the nose cone dilator 22 during insertion and delivery to the target site.

The stent graft 56 at the proximal end 4 of the delivery device 2 is fully sheathed and held in a radially inwardly contracted condition. When the position of the device 2 is satisfactory, the user may partially withdraw the sheath 28. The user retracts the sheath 28 by moving the proximal gripping portion 12 distally, towards the stationary gripping portion 10 along the longitudinal axis 34 to expose at least the proximal end 58 of the stent graft 56. Other visual or mechanical signals may also be present on the delivery device 2 and/or handle assembly 8 to indicate proper positioning of the stent graft 56 after the sheath 28 has been at least partially retracted. At this stage, the user continues to retract the sheath 28 by moving the proximal gripping portion 12 distally towards the stationary gripping portion 10 along the longitudinal axis 34 to expose at least a portion of the stent graft 56 distal to the already exposed proximal stent end.

Once the proximal gripping portion 12 has moved to its distal-most position where it is adjacent to and/or abuts the stationary gripping portion 10, the sheath 28 is therefore also fully retracted to expose the stent graft 56 while also moving the rails 14, 16, 18 distally with it. As such, the rails 14, 16, 18 extend behind (distal to) the stationary gripping portion 10 to provide a sufficient distal travel distance for the trigger wire release knobs 62, 64, 66 to slide longitudinally upon, in a distal direction, during trigger wire release and removal.

At this stage, the user can retract the first trigger wire release knob 62 (the distal-most knob) along the rails 14, 16, 18 in a distal direction until the first trigger wire release knob 62 reaches the end cap 26. Retraction of the first trigger wire release knob 62 serves to retract the first trigger wire and remove it from the proximal end of the stent graft 56, thus facilitating deployment of the proximal end 58 of the stent graft 56. The user may then manipulate the second trigger wire release knob 64 by sliding it longitudinally over the rails 14, 16, 18, in a distal direction, until the distal side of the second trigger wire release knob 64 abuts the proximal side of the first trigger wire release knob 62, or another predetermined stopping location. Retraction of the second trigger wire release knob 64 serves to retract the second trigger wire and remove it from the distal end 60 of the stent graft 56, thus facilitating deployment of the distal end 60 of the stent graft 56. The user can then manipulate the third trigger wire release knob 66 by sliding it longitudinally over the rails 14, 16, 18, in a distal direction, until the distal side of the third trigger wire release knob 66 abuts the proximal side of the second trigger wire release knob 64, or another predetermined stopping point. Retraction of the third trigger wire release knob 66 serves to retract the third trigger wire 86 and remove it from one or more diameter reducing ties as well as any additional attachment mechanisms, to allow the stent graft 56 to fully deploy within a vessel.

For this example, the delivery device 2 comprises three trigger wire release knobs 62, 64, 66, and three trigger wires, although it will be appreciated that more or fewer trigger wire release knobs and/or trigger wires may be used as necessary or desired, depending on the type or size of the stent graft being used and the particular procedure being performed, along with other factors.

Following deployment, and with the stent graft 56 released from the stent graft retention region 20, the user withdraws the delivery device 2 from the patient's body. Once the stent graft 56 has been fully released from the delivery device 2, the delivery device 2 is withdrawn distally. In some instances, if delivery of another stent graft is desired, a guide wire may be left in place, even after the delivery device 2 is removed from the vasculature, to facilitate tracking of another delivery device 2 for the delivery and deployment of another prosthesis and/or stent graft.

When removing the delivery device 2 from the patient, the user may optionally slide the proximal gripping portion 12 in a proximal direction, thus sliding the sheath 28 proximally and allowing the proximal end 30 of the sheath 28 to extend over all of, part of, or at least a distal portion of the nose cone dilator 22 of the device 2 so as to "hub" or "recapture" a portion of the nose cone 22 within the sheath 28. With at least a distal portion of the nose cone dilator 22 recaptured within the sheath 28, the delivery device 2 can be withdrawn from the patient's body to complete the procedure, thus having effectively and efficiently deployed a stent graft 56 into one or more vessels in order to treat and/or restore patency to such vessel(s).

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

The invention claimed is:

1. A handle assembly for a prosthesis delivery device, the handle assembly comprising:
   a proximal gripping portion,
   a stationary gripping portion,
   at least one rail extending distally from the proximal gripping portion,
   wherein the at least one rail extends through at least a portion of the stationary gripping portion,
   wherein the proximal gripping portion is distally moveable along a longitudinal axis towards the stationary gripping portion from a first pre-deployment position to a second position,
   wherein the at least one rail extends proximally from the stationary gripping portion when the proximal gripping portion is in a first pre-deployment position, and
   wherein the at least one rail extends distally from the stationary gripping portion when the proximal gripping portion is in a second position;
   wherein the at least one rail comprises a first rail, a second rail, and a third rail, and
   wherein the at least one of the first, second, third rails further comprises at least one predetermined breaking point and wherein the predetermined breaking point comprises at least one of a weakened portion of the at least one of the first, second, third rails and a separable joint.

2. The handle assembly of claim 1, wherein the proximal gripping portion is adjacent to the stationary gripping portion when the proximal gripping portion is in the second position.

3. The handle assembly of claim 1, wherein the first rail, the second rail, and the third rail are arranged about the longitudinal axis.

4. The handle assembly of claim 1, wherein a width of the third rail is greater than a width of the first rail and a width of the second rail.

5. The handle assembly of claim 1, wherein the at least one of the first, second, third rails operatively couples the stationary gripping portion to the proximal gripping portion.

6. The handle assembly of claim 1, wherein the at least one of the first, second, third rails is configured to prevent independent axial rotation of the proximal gripping portion about the longitudinal axis relative to the stationary gripping portion.

7. The handle assembly of claim 1, further comprising at least one trigger wire release mechanism disposed about the at least one of the first, second, third rails at a location distal to the stationary gripping portion.

8. The handle assembly of claim 7, wherein the at least one trigger wire release mechanism is longitudinally moveable along the at least one of the first, second, third rails when the proximal gripping portion is in the second position.

9. The handle assembly of claim 8, wherein longitudinal movement of the at least one trigger wire release mechanism is substantially prevented when the proximal gripping portion is in the first position.

10. The handle assembly of claim 7, wherein the at least one trigger wire release mechanism is distally slidable about an outer surface of the at least one of the first, second, third rails.

11. The handle assembly of claim 7, wherein the at least one trigger wire release mechanism further comprises a second trigger wire release mechanism and wherein the at least one trigger wire release mechanism and the second trigger wire release mechanism are sequentially moveable along the at least one of the first, second, third rails.

12. The handle assembly of claim 11, wherein movement of the second trigger wire release mechanism is prevented until the first trigger wire release mechanism is moved distally along the at least one of the first, second, third rails.

13. A delivery system for delivering a prosthesis, the delivery system comprising:
   an inner cannula having a proximal end and a distal end, wherein a prosthesis is releasably coupled to the proximal end of the inner cannula and a handle assembly is disposed about the distal end of the inner cannula, the handle assembly comprising:
   a proximal gripping portion and a stationary gripping portion and at least one rail extending distally from the proximal gripping portion,
   wherein the proximal gripping portion is longitudinally moveable towards the stationary gripping portion from a first pre-deployment position to a second position,
   wherein the at least one rail extends proximally from the stationary gripping portion when the proximal gripping portion is in a first pre-deployment position and
   wherein the at least one rail extends distally from the stationary gripping portion when the proximal gripping portion is in a second position,
   a sheath coupled to and extending proximally from the proximal gripping portion, wherein the sheath is disposed about the prosthesis when the proximal gripping portion is in the first pre-deployment position and wherein the sheath is retracted to expose at least a portion of the stent graft when the proximal gripping portion is in the second position;
   wherein the at least one rail comprises a first rail, a second rail, and a third rail, and
   wherein the at least one of the first, second, third rails further comprises at least one predetermined breaking point and wherein the predetermined breaking point comprises at least one of a weakened portion of the at least one of the first, second, third rails and a separable joint.

14. The delivery system of claim 13, wherein the at least one of the first, second, third rails is configured to prevent independent axial rotation of the handle assembly about the longitudinal axis relative to the prosthesis at the proximal end of the delivery device.

15. The delivery system of claim 13, wherein the at least one of the first, second, third rails is configured to prevent accumulation of torque along the inner cannula between the handle assembly and a nose cone dilator.

16. The delivery system of claim 13, further comprising at least one trigger wire release mechanism disposed about the at least one of the first, second, third rails at a location distal to the stationary gripping portion.

17. The delivery system of claim 16, wherein the at least one trigger wire release mechanism is longitudinally moveable along the at least one of the first, second, third rails when the proximal gripping portion is in the second position.

18. The delivery system of claim 17, wherein longitudinal movement of the at least one trigger wire release mechanism is substantially prevented when the proximal gripping portion is in the first pre-deployment position.

19. The delivery system of claim 16, wherein the at least one trigger wire release mechanism further comprises a second trigger wire release mechanism and wherein the at least one trigger wire release mechanism and the second trigger wire release mechanism are sequentially moveable along the at least one of the first, second, third rails, and wherein movement of the second trigger wire release mechanism is prevented until the first trigger wire release mechanism is moved distally along the at least one of the first, second, third rails.

20. A method for delivering an endovascular prosthesis comprising:
   providing a delivery device having a proximal end and a distal end, wherein a prosthesis is releasably coupled to the proximal end of a inner cannula and a handle assembly is disposed about a distal end of the inner cannula, the handle assembly comprising:
   a proximal gripping portion and a stationary gripping portion and at least one rail extending distally from the proximal gripping portion, wherein the proximal gripping portion is longitudinally moveable towards the stationary gripping portion from a first pre-deployment position to a second position, wherein the at least one rail extends proximally from the stationary gripping portion when the proximal gripping portion is in a first pre-deployment position and wherein the at least one rail extends distally from the stationary gripping portion when the proximal gripping portion is in a second position and wherein at least one trigger wire release mechanism is disposed upon the at least one rail,
   moving the proximal gripping portion from the first pre-deployment position to the second position to retract a sheath coupled to the proximal gripping portion and expose at least a portion of the prosthesis;
   moving a trigger wire release mechanism distally upon the at least one rail to retract and release at least one trigger wire from the prosthesis;
   wherein the at least one rail comprises a first rail, a second rail, and a third rail, and
   wherein the at least one of the first, second, third rails further comprises at least one predetermined breaking point and wherein the predetermined breaking point comprises at least one of a weakened portion of the at least one of the first, second, third rails and a separable joint.

* * * * *